US008684591B2

(12) United States Patent
Durchdewald et al.

(10) Patent No.: US 8,684,591 B2
(45) Date of Patent: Apr. 1, 2014

(54) AUTOMATED LABORATORY SYSTEM (75) Inventors: Michael Durchdewald, Kernen (DE); Herbert Schaffert, Talheim (DE); Thomas Brinz, Teck (DE); Karl-Heinz Effenberger, Schwaebisch Gmuend (DE); Klaus Prescha, Besigheim (DE); Olaf Elstert, Birenbach (DE); Joachim Kumle, Weil der Stadt (DE); Tobias Burk, Tuebingen (DE); Roland Emmerich, Beilstein (DE)

(73) Assignee: Robert Bosch GmbH, Stuttgart (DE)

( * ) Notice: Subject to any disclaimer, the term of this patent is extended or adjusted under 35 U.S.C. 154(b) by 876 days.

(21) Appl. No.: 12/876,712

(22) Filed: Sep. 7, 2010

(65) Prior Publication Data
US 2011/0085410 A1    Apr. 14, 2011

(30) Foreign Application Priority Data
Sep. 8, 2009 (DE) .......................... 10 2009 029 246

(51) Int. Cl.
*B01L 3/00* (2006.01)
*B01F 15/04* (2006.01)

(52) U.S. Cl.
USPC .............................. 366/141; 422/63; 422/509

(58) Field of Classification Search
USPC ............. 366/141; 422/64, 65, 509, 514, 521, 422/224, 225
See application file for complete search history.

(56) References Cited

U.S. PATENT DOCUMENTS

| 6,387,330 | B1 * | 5/2002 | Bova et al. | 422/509 |
|---|---|---|---|---|
| 6,548,026 | B1 * | 4/2003 | Dales et al. | 422/138 |
| 6,673,316 | B1 | 1/2004 | Okamoto et al. | |
| 6,752,960 | B1 * | 6/2004 | Matsubara et al. | 422/63 |
| 2009/0056477 | A1 * | 3/2009 | Nishimura et al. | 73/864.11 |

FOREIGN PATENT DOCUMENTS

| AU | 2002301520 | 6/2003 |
|---|---|---|
| DE | 197 49 557 | 5/1999 |
| EP | 0 918 221 | 5/1999 |
| GB | 2 440 932 | 2/2008 |
| WO | WO 01/03882 | 1/2001 |

* cited by examiner

*Primary Examiner* — Tony G Soohoo
(74) *Attorney, Agent, or Firm* — Kenyon & Kenyon LLP (57) ABSTRACT

An automated laboratory system, which includes a vessel supply rack for supplying vessels in a vessel supply position, a movable vessel pick-up table for picking up and moving a vessel from the vessel supply position to the vessel filling position, a movable metering table disposed above the vessel pick-up table and configured for picking up and moving at least two metering containers configured to hold chemical substances, the metering containers being able to be positioned above the vessel filling position to fill chemical substances into a vessel, a scale, disposed underneath the vessel filling position for determining a substance quantity filled into a vessel, and a stirrer, disposed above the vessel filling position, for mixing of substances filled into a vessel. Also described is a method for operating such a laboratory system.

12 Claims, 5 Drawing Sheets

Fig. 4

AUTOMATED LABORATORY SYSTEM

RELATED APPLICATION INFORMATION

The present application claims priority to and the benefit of German patent application no. 10 2009 029 246.2, which was filed in Germany on Sep. 8, 2009, the disclosure of which is incorporated herein by reference.

FIELD OF THE INVENTION

The present invention relates to an automated laboratory system and to a method for operating such a laboratory system.

BACKGROUND INFORMATION

In the high throughput technology, syntheses of new materials, formulations or substances that are otherwise performed manually, are automated. The laboratory systems used for this purpose frequently have various metering, mixing and process units and make it possible to produce samples of different compositions.

SUMMARY OF THE INVENTION

The subject matter of the exemplary embodiments and/or exemplary methods of the present invention is an automated laboratory system, which includes
  a vessel supply rack for supplying vessels in a vessel supply position;
  a movable vessel pick-up table for picking up and moving a vessel from the vessel supply position to a vessel filling position;
  a movable metering table disposed above the vessel pick-up table, for picking up and moving at least two metering containers configured to hold chemical substances, the metering containers being able to be positioned above the vessel filling position for filling, especially metering, chemical substances into a vessel;
  a scale, which is disposed underneath the vessel filling position or underneath a vessel situated in the vessel filling position, for determining, particularly controlling, a substance quantity filled into a vessel;
  a stirrer, situated above the vessel filling position or above a vessel situated in the vessel filling position, for mixing substances filled into a vessel.

In an advantageous manner, such a laboratory system may offer a simple and cost-effective automation approach for research featuring high throughput rates. In comparison with complex robots and axle systems, the use of movable tables advantageously makes it possible to provide a relatively robust and cost-effective automation approach that is not susceptible to malfunctions.

Furthermore, the filling/metering, weighing and stirring advantageously is performed in one location. In an advantageous manner, the vessel and the sample to be produced therein thus need not be moved from start to finish of the metering and mixing operations. Furthermore, in particular only one vessel or only one sample is able to be processed in each case. In other words, the sample may be removed, processed and then put aside. This has the advantage that it is not necessary to indicate a position of the vessel.

Such an automated laboratory system may be an automated synthesis-reactor system, in particular.

The laboratory system may be configured to process individual vessels.

The metering table may be moved to a first metering position, in which a first metering container is positioned above the vessel filling position. Furthermore, the metering table may be moved to a second metering position, in which a second metering container is positioned above the vessel filling position. In addition, the metering table is able to be moved to additional metering positions, in which other metering containers are positioned above the vessel filling position.

For example, the metering table may include at least three, e.g., at least four, especially at least five metering containers for holding chemical substances. The metering table is able to be moved to a third metering position, in which a third metering container is positioned above the vessel position, and/or to a fourth metering position, in which a fourth metering container is positioned above the vessel position, and/or to a fifth metering position, in which a fifth metering container is positioned above the vessel position, and so on.

Basically, the vessel pick-up table and the metering table may be configured as round tables or as linear tables, separately from each other.

Within the framework of one specific embodiment of the present invention, the vessel pick-up table is a round table, and/or the metering table is a round table. By combining two round tables, in particular combining them with simple rotary tables, it is possible to achieve fully flexible metering of chemical substances in random sequences, and thus to produce the most varied samples.

Within the framework of an additional specific embodiment of the present invention, the laboratory system includes a vessel opening device for opening a vessel which is in a vessel opening position. Toward this end, the vessel pick-up table may be configured to pick up and move a vessel from the vessel supply position to the vessel opening position, and/or from the vessel opening position to the vessel filling position.

Within the framework of a further specific embodiment of the present invention, the laboratory system includes a vessel sealing device for sealing a vessel disposed in the vessel sealing position. For this purpose the vessel pick-up table may be configured to pick up and move a vessel from the vessel filling position to the vessel sealing position.

Furthermore, the vessel pick-up table may be configured to pick up and move a vessel, in particular a single vessel, from the vessel filling position to a further processing position. For example, a device for heating and/or cooling, and/or analyzing the content of a vessel, in particular a single vessel, may be disposed in the further processing position. For instance, a device for analyzing may be a device for measuring the pH value and/or the viscosity and/or the surface tension and/or the clouding and/or particles.

The laboratory system is able to be connected to an additional automated laboratory system, e.g., an automated laboratory system of the same type, or to an automated laboratory having essentially the same type of design.

For instance, the laboratory system is able to be connected to an additional automated laboratory system, which
  has a movable vessel pick-up table for picking up a vessel, in particular from a concatenation position of the previous laboratory system, to a vessel supply position of the further laboratory system, and for moving a vessel from a vessel supply position to a vessel filling position;
  a movable metering table, disposed above the vessel pick-up table, for picking up and moving at least two metering containers configured to hold chemical substances, the metering containers being able to be positioned above the vessel filling position for filling, in particular metering, chemical substances into a vessel;

a scale, disposed underneath the vessel filling position or underneath a vessel disposed in the vessel filling position, for determining, in particular controlling, a chemical substance filled into a vessel; and a stirrer, disposed above the vessel filling position or a vessel situated in the vessel filling position, for mixing substances filled into a vessel.

The vessel pick-up table and the metering table of the additional laboratory system may have a design that resembles that of the first laboratory system. In particular, the vessel pick-up table and the metering table of the additional laboratory system may be round tables. The vessel pick-up table of the additional (second) laboratory system may, for example, likewise be connected to a still further (third) automated laboratory system, e.g., an automated laboratory system of the same type or an automated laboratory system of essentially the same type, and so on.

Within the framework of an additional specific embodiment of the present invention, the vessel pick-up table is configured for picking up and moving a vessel from the vessel filling position, optionally from the further processing position, to a concatenation position; from the concatenation position, a vessel is able to be transferred to a further laboratory system, and/or able to be returned from the additional laboratory system to the concatenation position of the previous laboratory system.

Within the framework of an additional specific embodiment of the present invention, the laboratory system includes a vessel dispensing rack for picking up and/or collecting vessels from a vessel dispensing position. For this purpose, the vessel pick-up table may be configured to pick up and move a vessel from the vessel filling position, optionally via the further processing position, and/or optionally via the concatenation position, and/or optionally via the vessel sealing position, to the vessel dispensing position.

Within the framework of a further specific embodiment of the present invention, the metering table includes at least one exchangeable metering container pick-up mechanism for picking up a metering container. The exchangeable metering container pick-up mechanism may be configured, for example, to pick up special solid matter metering containers, in particular powder metering containers, or to pick up special liquid metering containers. By exchanging an exchangeable metering container pick-up mechanism for picking up a special solid matter or fluid metering container for another exchangeable metering container pickup mechanism for picking up another special solid matter metering container or fluid metering container, the laboratory system is able to be refitted for different special solid matter or fluid metering containers in a simple manner.

As an alternative, however, the metering table may also include at least one fixedly installed or exchangeable metering vessel pick-up mechanism, which is adaptable to solid matter metering containers and/or fluid metering containers having different designs.

The stirrer of the laboratory system may be disposed above the vessel filling position in a manner that allows vertical movements. In this way, once a vessel has been positioned in the vessel filling position, the stirrer is able to be moved into a vessel in order to mix the chemical substances held in the vessel. Then, the stirrer may be moved out of the vessel again, and the vessel be moved to a different position by moving the vessel pick-up table.

Furthermore, the laboratory system may include a control device for controlling the vessel supply rack, the vessel pick-up table, the metering table, the metering container, the scale, the stirrer, optionally the vessel opening device, optionally the vessel sealing device, optionally the device positioned in the further processing position, optionally the further automated laboratory system and/or optionally the vessel dispensing rack.

In addition, the laboratory system may include a display and operating device, in particular a manually operable display and operating device, for displaying process parameters, and for operating, especially programming, the laboratory system of the control device, in particular.

The laboratory system may be integrated in a housing. The vessel dispensing rack and the optional vessel dispensing rack as well as the optional display and operating device may be accessible from outside the housing.

Furthermore, the housing may include a vertically movable cap. Such a cap may first be moved vertically in the upward direction, for example, in order to open the housing, e.g., in order to service or exchange devices disposed therein, such as metering containers and/or metering container pick-up mechanisms, and may then be moved vertically in the downward direction in order to reseal the housing. In particular, the cap may be made of a transparent material, so that the processing operation is able to be controlled visually from the outside. In addition, the cap may be made of an explosion-resistant material. In this way persons present in the vicinity of the laboratory system may advantageously be protected from injuries.

A metering device having a metering element may be used as vessel and/or as metering container, for example, whose metering element has a storage vessel for holding the substances to be metered and which is open on one side; in addition, it has a plug, which is axially movable and reversibly seals the opening of the storage vessel, and which may include, in the center, at least one metering orifice for metering substances held in readiness in the storage vessel, the storage vessel and/or the plug having a pick-up mechanism as engagement point for a mechanical gripping device. For example, the vessel pick-up table may engage with this pick-up mechanism.

Moreover, the supply vessel may have a pick-up mechanism on its boundary surface lying across from the orifice. The plug may be connected to a plunger rod, which has a metering line for metering stored substances and at whose end facing away from the plug, the pick-up mechanism is disposed. At its end facing away from the plug, the plunger rod may be connected to an exchangeable metering needle. The plunger rod is able to be connected to the metering needle by a Luer-lock seal. The pick-up mechanism may have a code in order to detect the volume or the diameter of the associated storage vessel.

For example, such metering devices are described in the printed publications DE 10 2004 030 155 A1, GB 2 415 423 A, GB 2 415 423 B, and U.S. Pat. No. 7,191,917 B2, whose disclosure is hereby explicitly incorporated, by reference. Such metering devices or syringes may advantageously be used for metering highly viscous substances, and for producing and delivering them.

A further subject matter of the present invention is a method for operating an automated laboratory system according to the present invention, which includes the following method steps:

a) Moving a vessel to the vessel supply position, in particular via the vessel supply rack;

b) Picking up and moving the vessel from the vessel supply position to the vessel filling position, in particular via the vessel pick-up table;

c) Positioning a metering container above the vessel in the vessel filling position, in particular by moving the metering table; and Filling chemical substances from the metering container positioned above the vessel, into the vessel; and Determining the substance quantity filled into the vessel, in particular using the scale;

d) Mixing the substances filled into the vessel, in particular using the stirrer.

The method steps c) and d) may be performed both simultaneously and sequentially.

In particular, the method allows only a single vessel to be processed in each case.

During the filling operation in method step c), a particular substance quantity may be filled in selectively, i.e. metered in addition. Whether the particular substance quantity was actually metered into the vessel is subsequently able to be checked by a weighing operation.

Within the framework of an additional specific embodiment of the present invention, in method step c), chemical substances are therefore metered into the vessel from the metering container positioned above the vessel, and the substance quantity metered into the vessel is checked. The metering may be performed gravimetrically and/or volumetrically. All metering processes may be checked by the scale.

Method step c), in particular, may include a plurality of method steps:

c1) Positioning a first metering container above the vessel in the vessel filling position, in particular by moving the metering table to a first metering position; and Filling chemical substances from the first metering container, positioned above the vessel, into the vessel; and Determining the substance quantity filled into the vessel from the first metering container, in particular using the scale; and c2) Positioning a second metering container above the vessel in the vessel filling position, in particular by moving the metering table to a second metering position; and Filling chemical substances from the second metering container disposed above the vessel, into the vessel; and Determining the substance quantity filled from the second metering container into the vessel, in particular with the aid of the scale.

Furthermore, especially by moving the metering table to other metering positions, other metering containers are able to be positioned above the vessel in the vessel filling position.

For instance, in subsequent method steps c3), c4), c5) and so on, a third, fourth, fifth etc. metering container is able to be positioned above the vessel in the vessel filling position, in particular by moving the metering table to a third, fourth, fifth etc. metering position, and chemical substances from the third, fourth, fifth etc. metering container positioned above the vessel are able to be filled into the vessel, and the substance quantity filled into the vessel from the third, fourth, fifth etc. metering container is able to be determined, especially with the aid of the scale.

Within the framework of an additional specific embodiment of the present invention, the vessel is opened during method step b), in particular by a vessel opening device.

This may be done, for example, by moving the vessel in method step b) from the vessel supply position via a vessel opening position, to the vessel filling position, the vessel being opened in the vessel opening position.

Within the framework of an additional specific embodiment of the present invention, the method also includes method step e): Further processing of substances filled into the vessel. For instance, this may be done by moving the vessel, in particular by the vessel pick-up table, from the vessel filling position to an additional processing position, the substances filled into the vessel being processed further, such as heated and/or cooled and/or analyzed. During the analyzing, for example, the ph value, for instance, and/or the viscosity, and/or the surface tension, and/or the clouding and/or the particles are/is able to be measured.

Within the framework of a further specific embodiment of the present invention, the method also includes the method step f): transferring the vessel to a further laboratory system and/or returning the vessel from the additional laboratory system, to the previous laboratory system. For example, this could be done by moving the vessel, in particular with the aid of the vessel pick-up table, from the vessel filling position, optionally from the further processing position, to a concatenation position, the vessel being transferred in the concatenation position to a further laboratory system, and/or being returned from the additional laboratory system to the previous laboratory system.

Within the framework of a further specific embodiment of the present invention, the method also includes method step g): Sealing the vessel, in particular by a vessel sealing device. For example, this may be done by moving the vessel, in particular with the aid of the vessel pick-up table, from the vessel filling position to a vessel sealing position, the vessel being sealed in the vessel sealing position.

Within the framework of a further specific embodiment of the present invention, the method also includes method step h): Picking up and/or collecting vessels dispensed in a vessel dispensing position, in particular by a vessel dispensing rack. This may be done, for example, by moving the vessel, in particular with the aid of the vessel pick-up table, from the vessel filling position, optionally via the additional processing position and/or optionally via the concatenation position, and/or optionally via the vessel sealing position, to the vessel dispensing position, the vessel being picked up and/or collected from the vessel dispensing position by a vessel dispensing rack.

Within the framework of a further specific embodiment of the present invention, the method also includes method step f): Exchanging an exchangeable metering container pick-up mechanism for picking up a special solid matter or fluid metering container, for another exchangeable metering container pick-up mechanism for picking up a different special solid matter metering container or fluid metering container. In this way, the laboratory system is able to be refitted for different special solid matter or fluid metering containers in an uncomplicated manner.

Additional advantages and advantageous developments of the subject matters according to the present invention are illustrated by the drawing and explained in the following description. It should be noted that the figures are only of exemplary nature and are not meant to restrict the present invention in any way.

DETAILED DESCRIPTION

Figure 1:
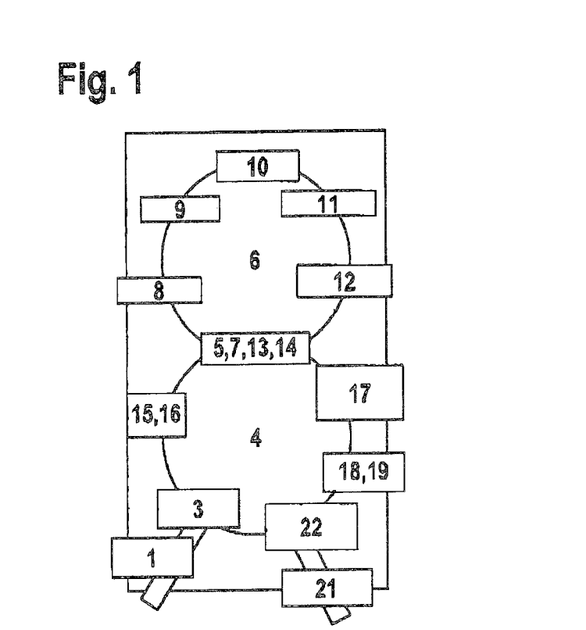
FIG. 1 shows a diagram for illustrating a first specific embodiment of the laboratory system according to the present invention.

FIG. 1 illustrates a first specific embodiment of the automated laboratory system according to the present invention, which includes a vessel supply rack 1 for supplying vessels (not shown in FIG. 1) to a vessel supply position 3, a movable vessel pick-up table 4, configured in the form of a round table, for picking up and moving a vessel from vessel supply position 3 to a vessel filling position 5, a movable metering table 6 positioned above vessel pick-up table 4, and configured in the shape of a round table. FIG. 1 illustrates that metering table 6 is able to pick up and move six metering containers 7-11 for holding chemical substances. Metering containers 7-11 are able to be positioned above vessel filling position 5 one after the other in order to fill chemical substances into a vessel. FIG. 1 indicates that a scale 13 for determining a substance quantity filled into a vessel is provided as well in the laboratory system, as is a stirrer 14 for mixing substances filled into a vessel, scale 13 being disposed underneath vessel filling position 5, and stirrer 14 above vessel filling position 5. FIG. 1 illustrates that in such a design it is possible that only one metering container 7-11 is disposed above vessel filling position 5 depending on the rotated position of the metering table. In particular, FIG. 1 shows metering table 6 in a first metering position, in which a first metering container 7 is positioned above vessel filling position 5. By moving, particularly rotating, metering table 6 to a second, third, fourth, fifth or sixth metering position, a second 8, third 9, fourth 10, fifth 11, or sixth 12 metering container may be positioned above vessel filling position 5.

In addition, FIG. 1 shows that the laboratory system also includes a vessel opening device 15 for opening a vessel positioned in a vessel opening position 16. Vessel pick-up table 4 is configured to pick up and move a vessel from vessel supply position 3 to vessel opening position 16, and from a vessel opening position 16 to a vessel filling position 5.

Furthermore, FIG. 1 illustrates that the laboratory system includes a vessel sealing device 17 for sealing a vessel 2 disposed in a vessel sealing position 18. In this context, vessel pick-up table 4 is configured to pick up and move a vessel from vessel filling position 5 to vessel sealing position 18.

Moreover, FIG. 1 shows that vessel pick-up table 4 is configured to pick up and move a vessel from vessel filling position 5 to a further processing position 17. A device for heating and/or cooling, and/or analyzing the content of a vessel, for example, may be disposed in the further processing position.

In addition, FIG. 1 illustrates that the laboratory system has a vessel dispensing rack 21 for picking up and collecting vessels dispensed from a vessel dispensing position 22. Vessel pick-up table 4 is configured to pick up and move a vessel from vessel filling position 5, via further processing position 17 and via vessel sealing position 19, to vessel dispensing position 22.

Furthermore, FIG. 1 illustrates that all metering steps 7-12 as well as weighing 13 and mixing 14 are performed at one location. All processes are arranged such that the sample to be produced and its vessel need not be moved until the metering and mixing has been completed. All metering processes are able to be checked with the aid of a scale.

Figure 2:
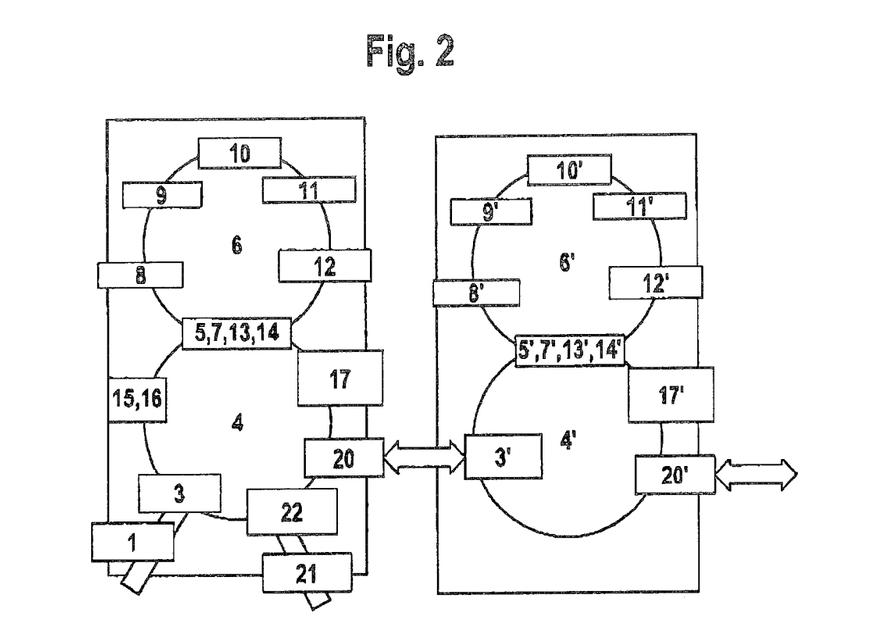
FIG. 2 shows a diagram for illustrating a second specific embodiment of the laboratory system according to the present invention.

FIG. 2 illustrates a second specific embodiment of the laboratory system, in which an additional, essentially similar automated laboratory system is connected. FIG. 2 shows that vessel pick-up table 4 is configured to pick up and move a vessel from vessel filling position 5 via additional processing position 17, to a concatenation position 20. From concatenation position 20, the vessel is transferred to vessel supply position 3' of the additional laboratory system. FIG. 2 shows that the additional laboratory system also includes a movable vessel pick-up table 4' for picking up the vessel from a concatenation position 20 of the previous laboratory system, to a vessel supply position 3', and for moving the vessel from a vessel supply position 3' to a vessel filling position 5', a movable metering table 6' disposed above vessel pick-up table 4' for picking up and moving six metering containers 7'-12' configured to hold chemical substances, a scale 13', disposed underneath vessel filling position 5' for determining a substance quantity filled into the vessel, and a mixer 14' disposed above vessel filling position 5', for mixing substances filled into a vessel. Furthermore, FIG. 2 shows that metering containers 7'-12' of the additional laboratory system are able to be positioned above vessel filling position 5' in order to fill chemical substances into a vessel. After running through the additional laboratory system, the vessel may be returned to the previous laboratory system again. However, the additional automated laboratory system may in turn also be connected to additional laboratory system, via an additional concatenation position 20'.

Figure 3A:
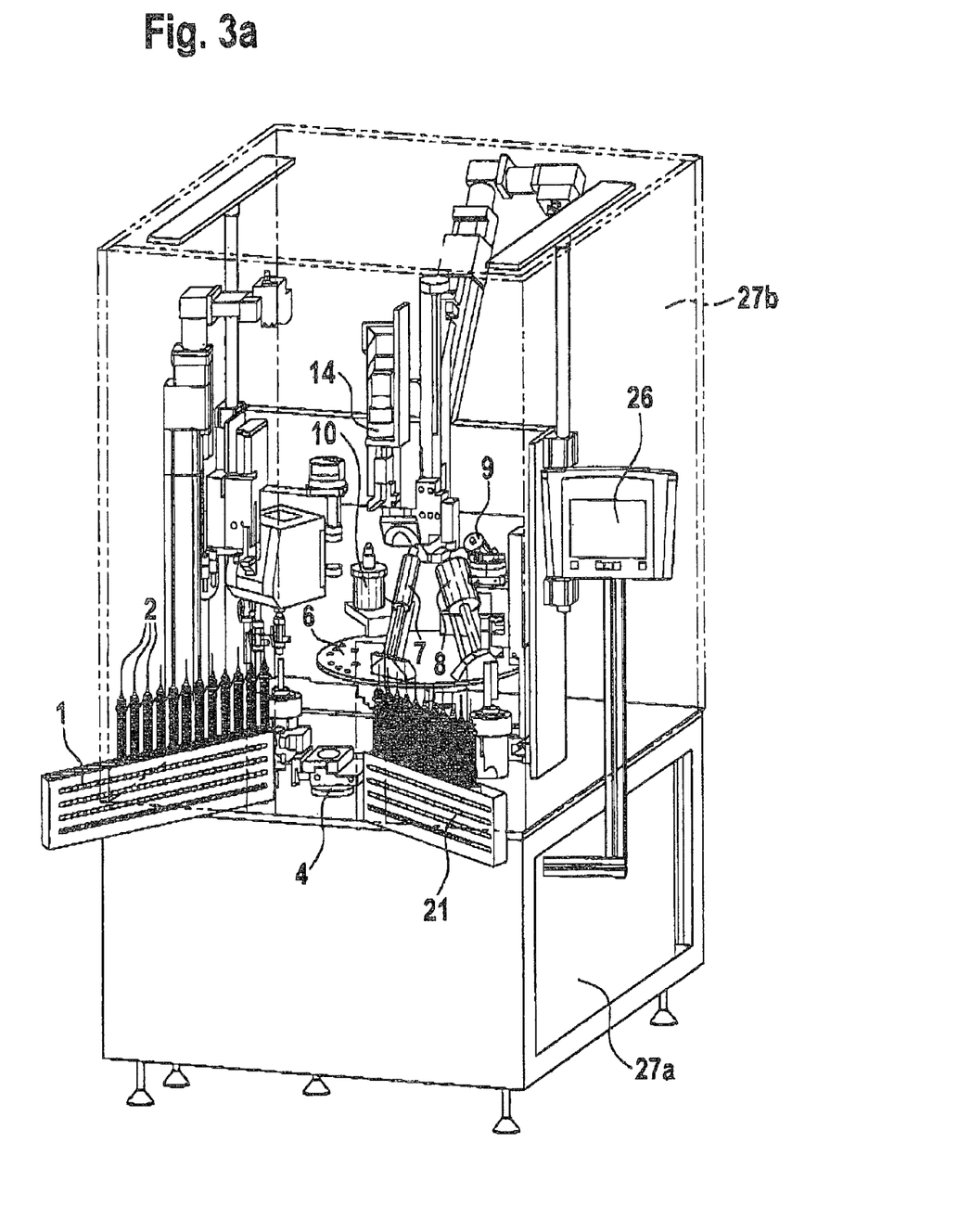
FIG. 3a shows a schematized, perspective view of a third specific embodiment of the laboratory system according to the present invention, having a closed cap.
Figure 3B:
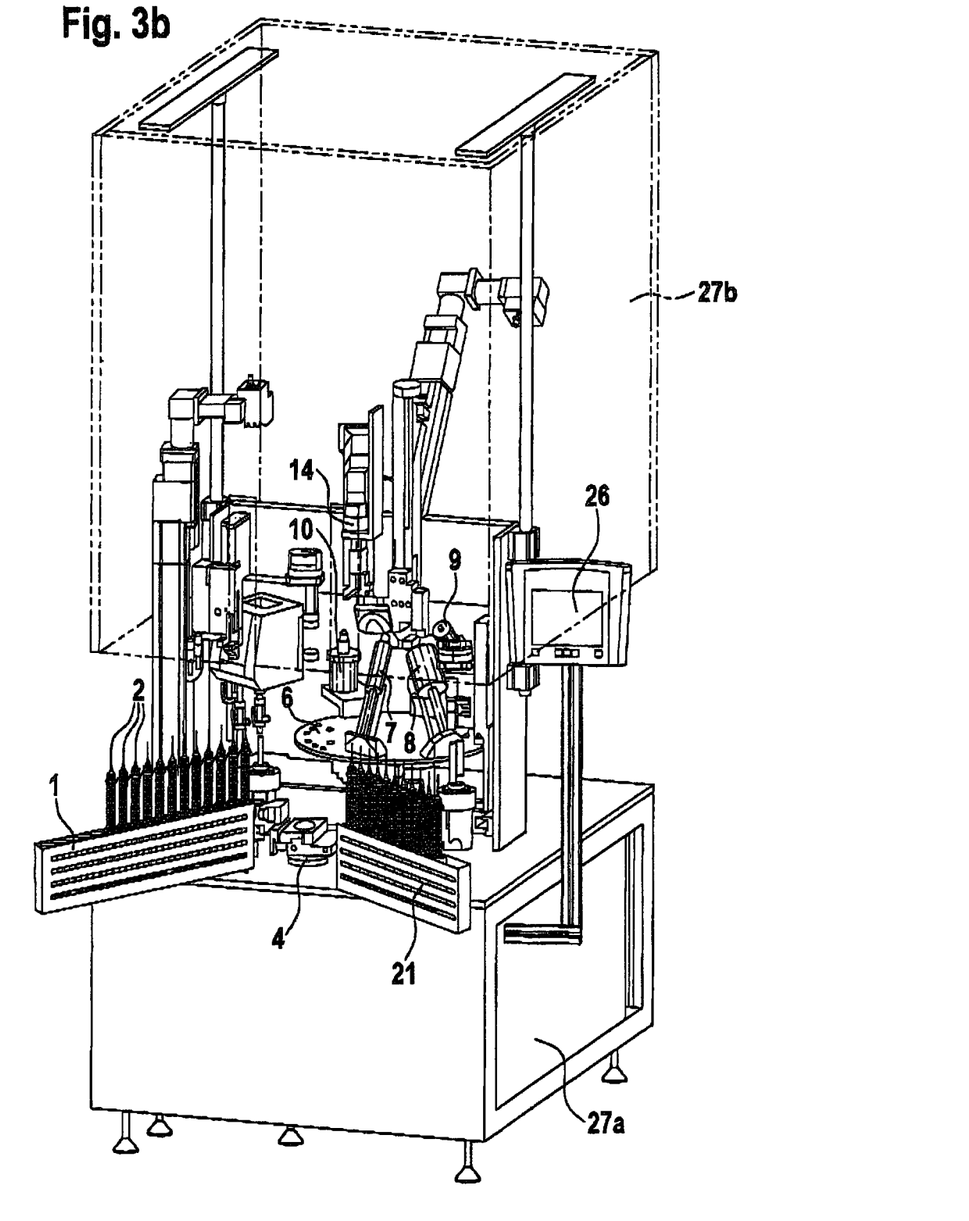
FIG. 3b shows a schematized, perspective view of the third specific embodiment, shown in FIG. 3a, of the laboratory system according to the present invention, having an opened cap.
Figure 3C:
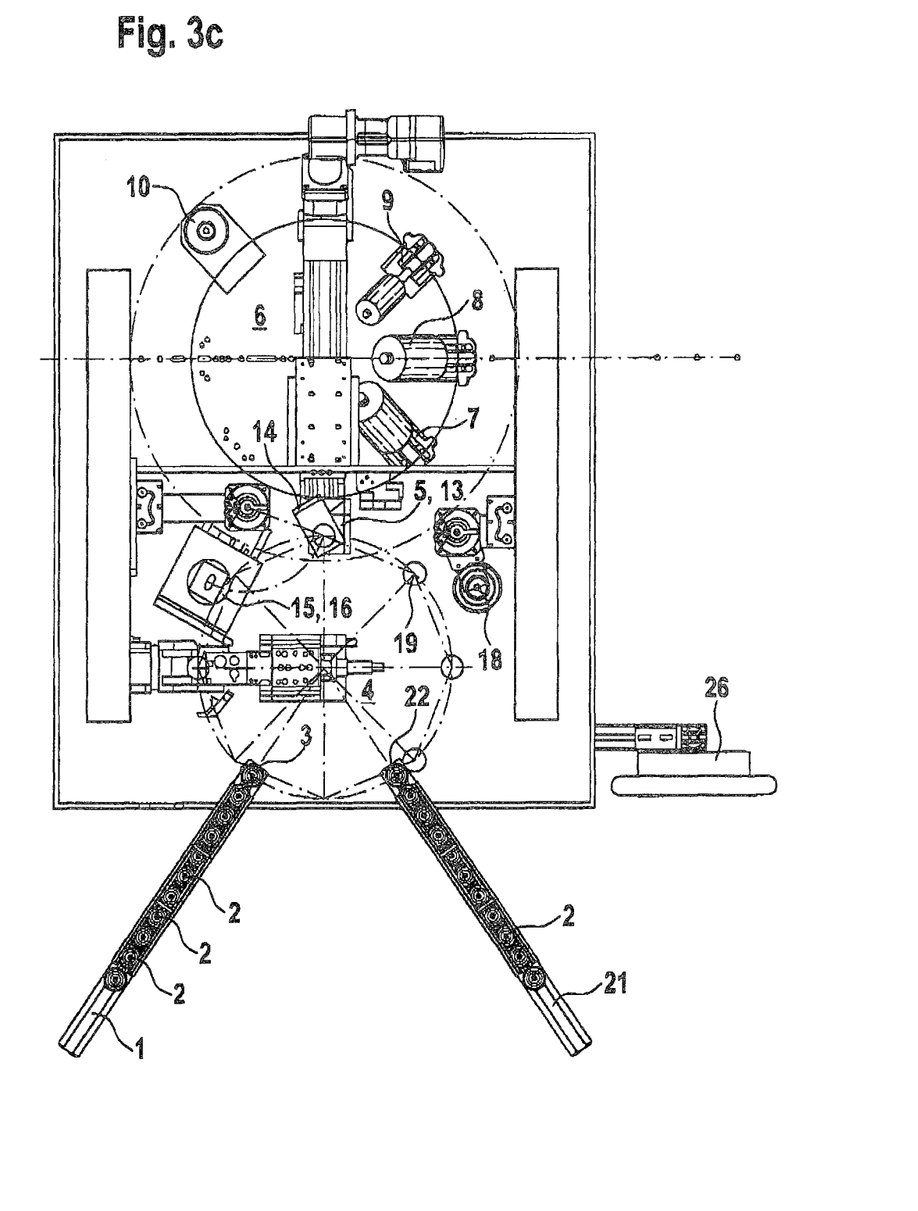
FIG. 3c shows a schematized plan view of the third specific embodiment, shown in FIGS. 3a and 3b, of the laboratory system according to the present invention.

FIGS. 3a through 3c show a third specific embodiment of the laboratory system according to the present invention. FIGS. 3a and 3b illustrate that the laboratory system also includes a vessel dispensing rack 21 and a display and operating device 26, and is integrated in a housing 27a, 27b, vessel supply rack 1, vessel dispensing rack 21, and display and operating device 26 being accessible from outside housing 27a, 27b. Furthermore, FIGS. 3a and 3b indicate that housing 27a, 27b has a vertically displaceable, transparent cap 27b, which is able to be moved in an upward direction in order to open housing 27a, 27b, and is able to be moved in a downward direction in order to seal housing 27a, 27b. FIGS. 3a and 3b also illustrate that syringe-type metering devices are able to be used as vessels 2. Vessels 2 are supplied in the closed state by vessel supply rack 1, then opened by vessel opening device 15, such as unscrewed, and then resealed again by a vessel sealing device 18 once the processing has been completed. Thus, a separate supply of seals may advantageously be dispensed with.

FIG. 3c once again illustrates in detail that vessel supply rack 1 supplies individual vessels 2 to a vessel supply position 3. Movable vessel pick-up table 4 picks up a single vessel 2 in each case and moves it from vessel supply position 3, in particular via a vessel opening position 16, in which individual vessel 2 is opened by a vessel opening device 15, to a vessel filling position 5. A movable metering table 6, which has at least three metering containers 7, 8, 9, 10, which are able to be individually positioned above vessel filling position 5 by moving metering table 6, is disposed above vessel pick-up table 4 in order to fill chemical substances into a single vessel 2 situated in vessel filling position 5. In addition, FIG. 3c illustrates that a scale 13 for determining a single substance quantity filled into an individual vessel 2 situated in vessel filling position 5 is disposed underneath vessel filling position 5. Moreover, FIG. 3c shows that a stirrer 14 for mixing substances filled into an individual vessel 2 situated in vessel filling position 5 is disposed above vessel filling position 5. In addition, FIG. 3c shows that the laboratory system includes a vessel sealing device 18 for sealing an individual vessel 2 disposed in a vessel sealing position 19, vessel pick-up table 4 being configured for picking up and moving a single vessel 2 from vessel filling position 5 to vessel sealing position 19. Furthermore, FIG. 3c shows that the laboratory system includes a vessel dispensing rack 21 for picking up and collecting individual vessels 2 dispensed from a vessel dispensing position 22, vessel pick-up table 4 being configured for picking up and moving a vessel 2 from vessel filling position 5, in particular via vessel sealing position 19, to vessel dispensing position 22.

Figure 4:
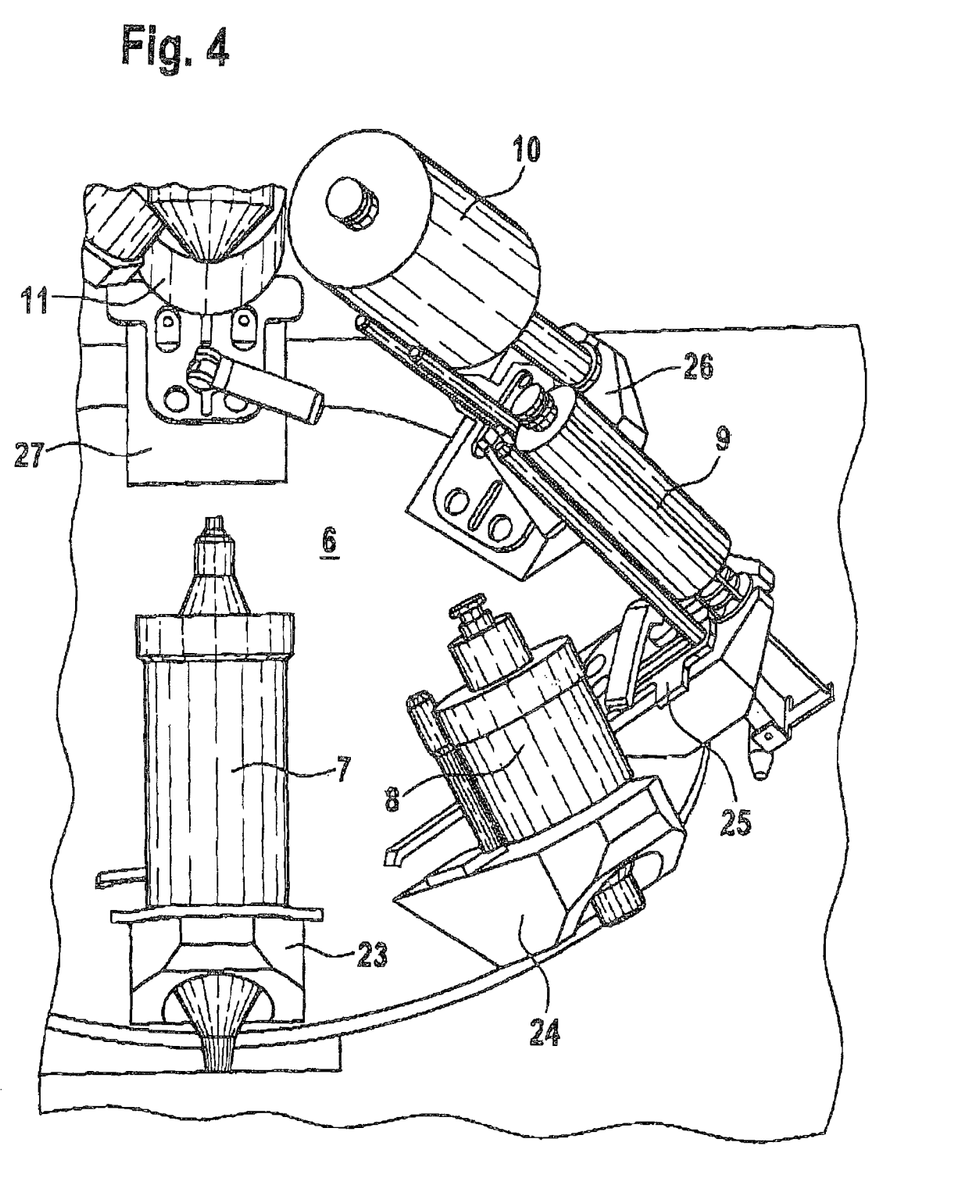
FIG. 4 shows a schematized, perspective view of a specific embodiment of a metering table having exchangeable metering container pick-up mechanisms.

FIG. 4 is a schematized, perspective view of one specific embodiment of a metering table 6 having exchangeable metering container pick-up mechanisms 23, 24, 25, 26, 27 for picking up special metering containers 7, 8, 9, 10, 11. The two front metering containers 7 and 8 are powder metering containers having different sizes (80 ml, 200 ml). Rear metering container 9 is a fluid syringe (300 ml). By simple exchange of the metering container pick-up plates 23, 24, 25, it is advantageously possible to meter from any position from any metering substance containers. For example, by exchanging metering container pick-up plates 23, 24, 25, both fluids and powders are able to be metered from the same position. Thus, the selection of the chemical substances is able to be adapted to the most varied sample requirements in a very flexible manner.

What is claimed is:

1. An automated laboratory system, comprising:
    a vessel supply rack for supplying vessels to a vessel supply position;
    a movable vessel pick-up table for picking up and moving a vessel from the vessel supply position to a vessel filling position;
    a movable metering table disposed above the vessel pick-up table, for picking up and moving at least two metering containers configured to hold chemical substances, the metering containers being positionable above the vessel filling position to fill chemical substances into a vessel;
    a scale disposed underneath the vessel filling position, for determining a substance quantity filled into a vessel; and
    a stirrer disposed above the vessel filling position, for mixing substances filled into a vessel.

2. The laboratory system of claim 1, wherein at least one of the vessel pick-up table and the metering table is a round table.

3. The laboratory system of claim 1, wherein at least one of the following is satisfied (a) the laboratory system includes a vessel opening device for opening a vessel disposed in a vessel opening position, the vessel pick-up table being configured for picking up and moving a vessel at least one of (i) from the vessel supply position to the vessel opening position, and (ii) from the vessel opening position to the vessel filling position, and (b) the laboratory system includes a vessel sealing device for sealing a vessel disposed in the vessel sealing position, the vessel pick-up table being configured for picking up and moving a vessel from the vessel filling position to the vessel sealing position.

4. The laboratory system of claim 1, wherein the vessel pick-up table is configured for picking up and moving a vessel from at least one of the vessel filling position and the further processing position, to a concatenation position, a vessel being transferrable from the concatenation position to a further laboratory system, and/or to be returned from the further laboratory system to the concatenation position of the previous laboratory system.

5. The laboratory system of claim 1, wherein the laboratory system includes a vessel dispensing rack for at least one of picking up and collecting vessels dispensed from a vessel dispensing position, the vessel pick-up table being configured for picking up and moving a vessel from the vessel filling position, including via optionally at least one of via the additional processing position, the concatenation position, and the vessel sealing position, to the vessel dispensing position.

6. The laboratory system of claim 1, wherein the metering table includes at least one exchangeable metering container pick-up mechanism for picking up a metering container.

7. A method for operating an automated laboratory system, the method comprising:
    a) supplying a vessel to a vessel supply position of the automated laboratory system, which includes:
        a vessel supply rack for supplying vessels to the vessel supply position,
        a movable vessel pick-up table for picking up and moving a vessel from the vessel supply position to a vessel filling position,
        a movable metering table disposed above the vessel pick-up table, for picking up and moving at least two metering containers configured to hold chemical substances, the metering containers being positionable above the vessel filling position to fill chemical substances into a vessel,
        a scale disposed underneath the vessel filling position, for determining a substance quantity filled into a vessel, and
        a stirrer disposed above the vessel filling position, for mixing substances filled into a vessel;
    b) picking up and moving a vessel from the vessel supply position to the vessel filling position;
    c) positioning a metering container above the vessel in the vessel filling position, and filling chemical substances from the metering container positioned above the vessel, into the vessel and determining the substance quantity filled into the vessel; and
    d) mixing the substances filled into the vessel.

8. The method of claim 7, wherein, in method operation c), chemical substances are metered into the vessel from the metering container positioned above the vessel and the substance quantity metered into the vessel is checked.

9. The method of claim 7, wherein the vessel is opened during the method operation b).

10. The method of claim 7, the method further comprising:
    f) at least one of transferring the vessel to a further laboratory system and returning the vessel from the further laboratory system to the previous laboratory system.

11. The method of claim 7, the method further comprising:
    g) sealing the vessel.

12. The method of claim 7, the method further comprising:
    h) at least one of picking up and collecting vessels dispensed from a vessel dispensing position.

* * * * *